United States Patent

Flower

[11] Patent Number: 5,830,175
[45] Date of Patent: Nov. 3, 1998

[54] IONTOPHORETIC DRUG DELIVERY SYSTEM, INCLUDING DISPOSABLE PATCH

[75] Inventor: Ronald J. Flower, Vernon, N.J.

[73] Assignee: Becton Dickinson and Company, Franklin Lakes, N.J.

[21] Appl. No.: 899,429

[22] Filed: Jul. 24, 1997

Related U.S. Application Data

[63] Continuation of Ser. No. 535,604, Sep. 28, 1995, abandoned.

[51] Int. Cl.$^6$ .................................................... A61N 1/30
[52] U.S. Cl. .............................................. 604/20; 604/49
[58] Field of Search ........................... 604/20–21, 890.1, 604/49; 607/115

[56] References Cited

U.S. PATENT DOCUMENTS

| | | | |
|---|---|---|---|
| 4,622,031 | 11/1986 | Sibalis | 604/20 |
| 5,125,894 | 6/1992 | Phipps et al. | 604/20 |
| 5,135,479 | 8/1992 | Sibalis et al. | 604/20 |
| 5,156,591 | 10/1992 | Gross et al. | 604/20 |
| 5,160,316 | 11/1992 | Henley . | |
| 5,224,928 | 7/1993 | Sibalis et al. | 604/20 |
| 5,498,235 | 3/1996 | Flower . | |

FOREIGN PATENT DOCUMENTS

| | | |
|---|---|---|
| 0652135 | 6/1991 | Australia . |
| 0 060 452 | 9/1982 | European Pat. Off. . |
| 0 337 642 | 10/1989 | European Pat. Off. . |
| 0 461 680 | 12/1991 | European Pat. Off. . |
| 40 28 125 | 7/1991 | Germany . |
| 2 239 803 | 7/1991 | United Kingdom . |
| 860768 | 12/1986 | WIPO . |
| WO 92/04937 | 4/1992 | WIPO . |
| WO 93/11830 | 6/1993 | WIPO . |

Primary Examiner—Mark Bockelman
Attorney, Agent, or Firm—Allen W. Wark; Susan A. Capello

[57] ABSTRACT

An iontophoretic drug delivery system of the present invention includes a disposable patch electrically interconnectible with a controller. The patch includes at least two electrode assemblies, with one of the electrode assemblies having a first electrode and a second electrode. In this way, during delivery of electrical current one of the electrodes is exhausted so that upon an attempt to reuse the patch, the controller does not detect the delivery of electrical current through said electrodes and fails to supply electrical current to the electrode assemblies for delivery of the drug. Electrical interconnection between the patch and the controller is established by inserting a tab extending from the patch into the controller.

11 Claims, 4 Drawing Sheets

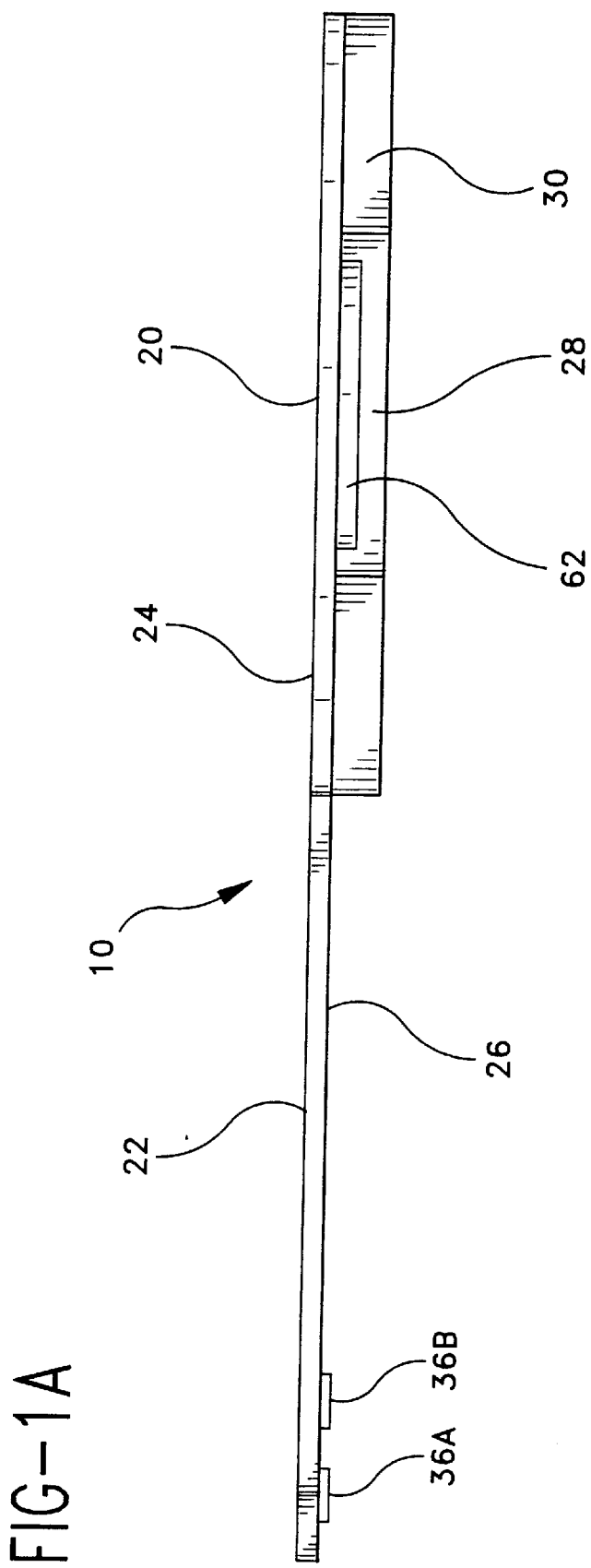

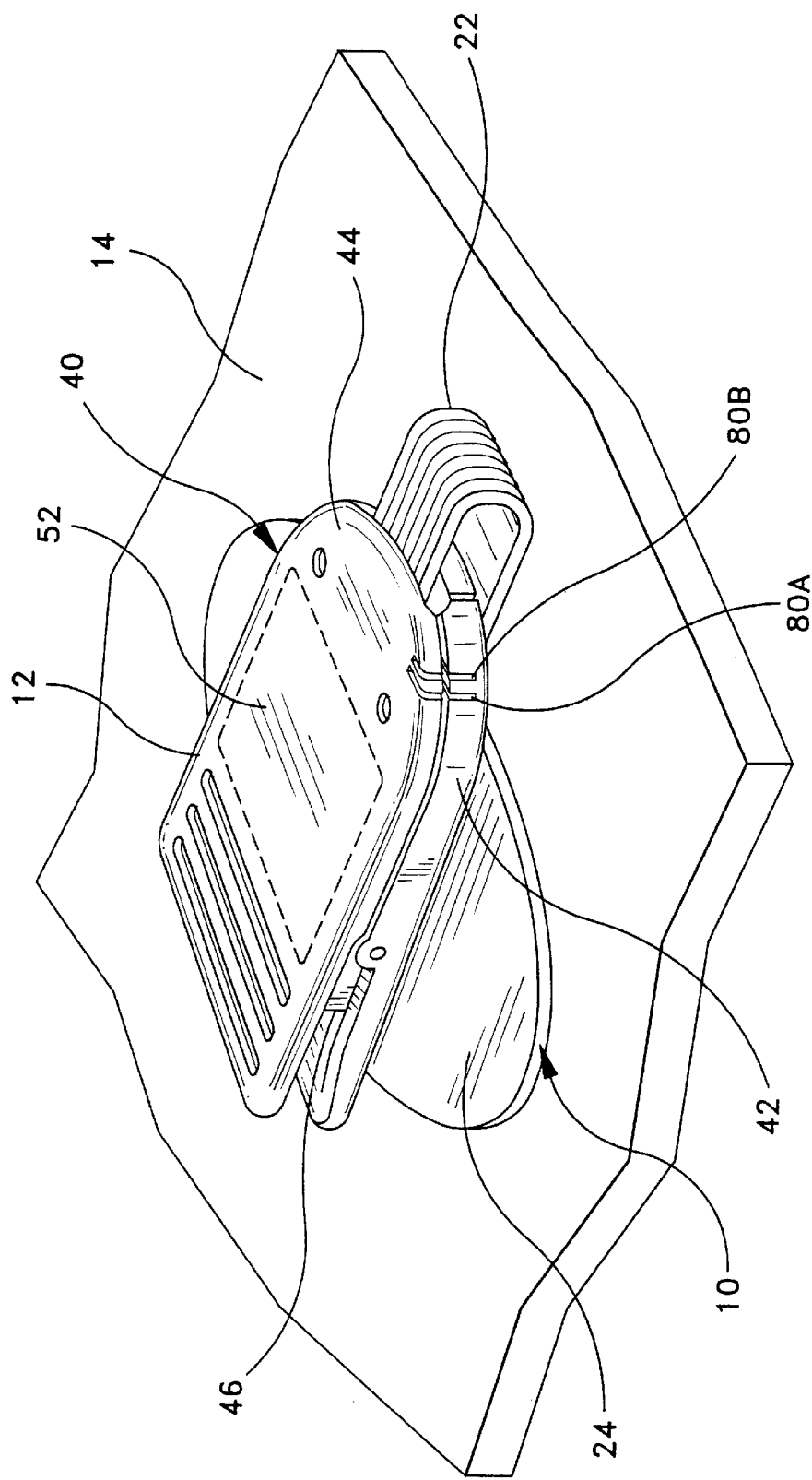

IONTOPHORETIC DRUG DELIVERY SYSTEM, INCLUDING DISPOSABLE PATCH

This application is a continuation of application Ser. No. 08/535,604, filed Sep. 9, 1995 now abandoned.

FIELD OF THE INVENTION

The present invention generally relates to iontophoretic drug delivery systems for delivering drugs, medicines, medicaments and the like to patients transdermally, i.e., through the skin, and more specifically relates to a disposable patch interconnectible with a controller.

BACKGROUND OF THE INVENTION

Transdermal drug delivery systems have, in recent years, become an increasingly important means of administering drugs and like therapeutic agents.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament." Such systems offer advantages clearly not achievable by any other methods of administration, such as avoiding introduction of the drug through the gastrointestinal tract or punctures in the skin to name a few.

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoretically delivered is negatively charged, the cathode will be the active electrode and the anode will be the counter electrode.

In practice, this process is typically achieved by placing the ionic drug either in solution or in gel form on a carrier and placing the drug-containing carrier, for example, in the form of a drug-filled adhesive patch, into contact with the skin. The pair of electrodes is placed in contact with the skin and with the carrier. Direct current is applied between the two electrodes. Under the influence of the electric field present, the drug molecules migrate through the skin. As current flows between the two electrodes placed at spaced apart locations on the skin, the current path carries the drug with it.

In order to deliver the drug to the patient, the adhesive patch may be applied to the desired portion of the patient's body and the controller attached to the patch. Oftentimes the controller is as large as, or larger than, the patch. It also should be somehow secured in place on the patient so that the patient may remain mobile and carry both the patch and controller with him as he moves about.

However, in situations where the iontophoretic device is to be applied by the patient, or the device is to be used by a health care professional with a multitude of patients, it would be helpful to such users to be able to insure that the device, particularly the drug-filled patch, has not been previously used so that the patient actually receives the proper amount of drug. For example, it would be beneficial if the device could communicate to the user whether the device is operational and whether it is actually delivering the drug to the patient.

Thus, there has been a need for an iontophoretic drug delivery system, particularly a disposable patch which would eliminate the problems and limitations associated with the prior devices discussed above, most significant of the problems being associated with attempts to reuse a patch.

SUMMARY OF THE INVENTION

In contrast to the prior devices and systems discussed above, it has been found that a iontophoretic drug delivery system including a disposable patch which may be constructed in accordance with the present invention is particularly suited for preventing reuse of a patch. In addition, the disposable patch of the present invention preferably can be easily attached to the controllers for delivering the drug, medicine, medicament or the like.

The disposable patch of the present invention for use in combination with a controller to form an operable iontophoretic drug delivery system includes a planar body portion including at least a first electrode assembly and a second electrode assembly, and the first electrode assembly having a first electrode and a second electrode both in contact with and adjacent to a drug filled reservoir, whereby when the patch is electrically connected to the controller, electrical current initially flows through the first electrode assembly from the second electrode to the first electrode and thereafter from the second electrode assembly to the first electrode.

In the preferred embodiment, the disposable patch further includes electrical interconnection means for interconnecting the body portion with a controller. Also, the body portion includes a tab having a plurality of electrical traces thereon in electrical communication with the electrode assemblies and the electrical interconnection means. In addition, at least one of the electrical traces interconnecting the first electrode and interconnectible with the electrical interconnection means includes a resistor.

The iontophoretic drug delivery system of the present invention includes a drug-filled patch removably attachable to the skin of a patient for iontophoretically delivering at least one drug to the patient, with the patch including electrical interconnection means for interconnecting the patch with the controller, a controller removably, electrically connectible to the patch, the controller providing sufficient energy to the patch to drive the ionized medicament into the skin of the patient and the controller including electronic means for monitoring and controlling electrical current supplied to the patch, and the patch including at least a first electrode assembly and a second electrode assembly, with the first electrode assembly having a first electrode and a second electrode both in contact with and adjacent to a drug filled reservoir, whereby when the patch is electrically connected to the controller, electrical current initially flows through the first electrode assembly from the second electrode to the first electrode and thereafter from the second electrode assembly to the first electrode.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 1A is a side view of the patch shown in FIG. 1;

FIG. 3 is a perspective view of the patch and controller attached to the skin of a patient.

DETAILED DESCRIPTION OF THE PREFERRED EMBODIMENT

Figure 1:
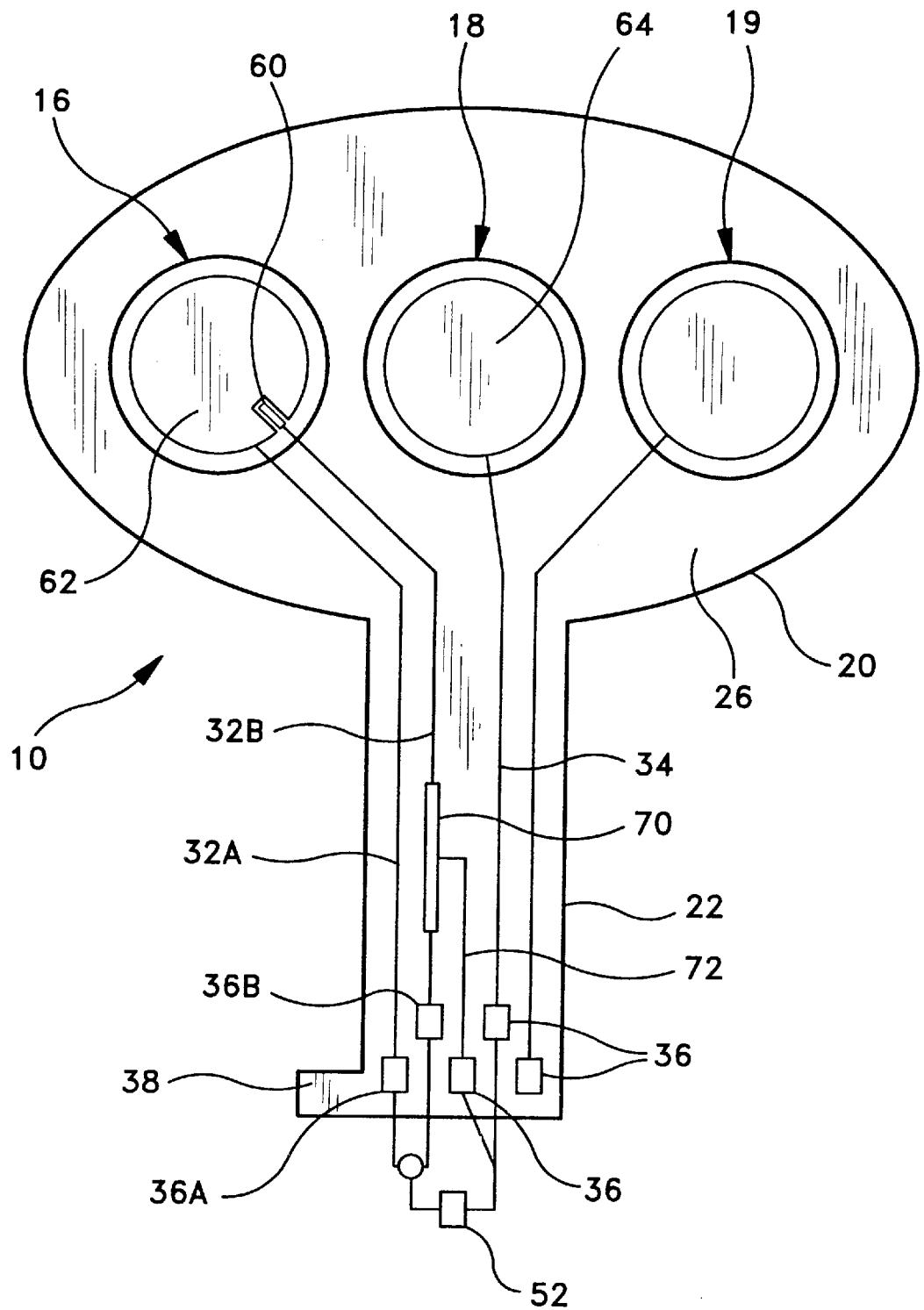
FIG. 1 is top view of the patch of the present invention.
Figure 2:
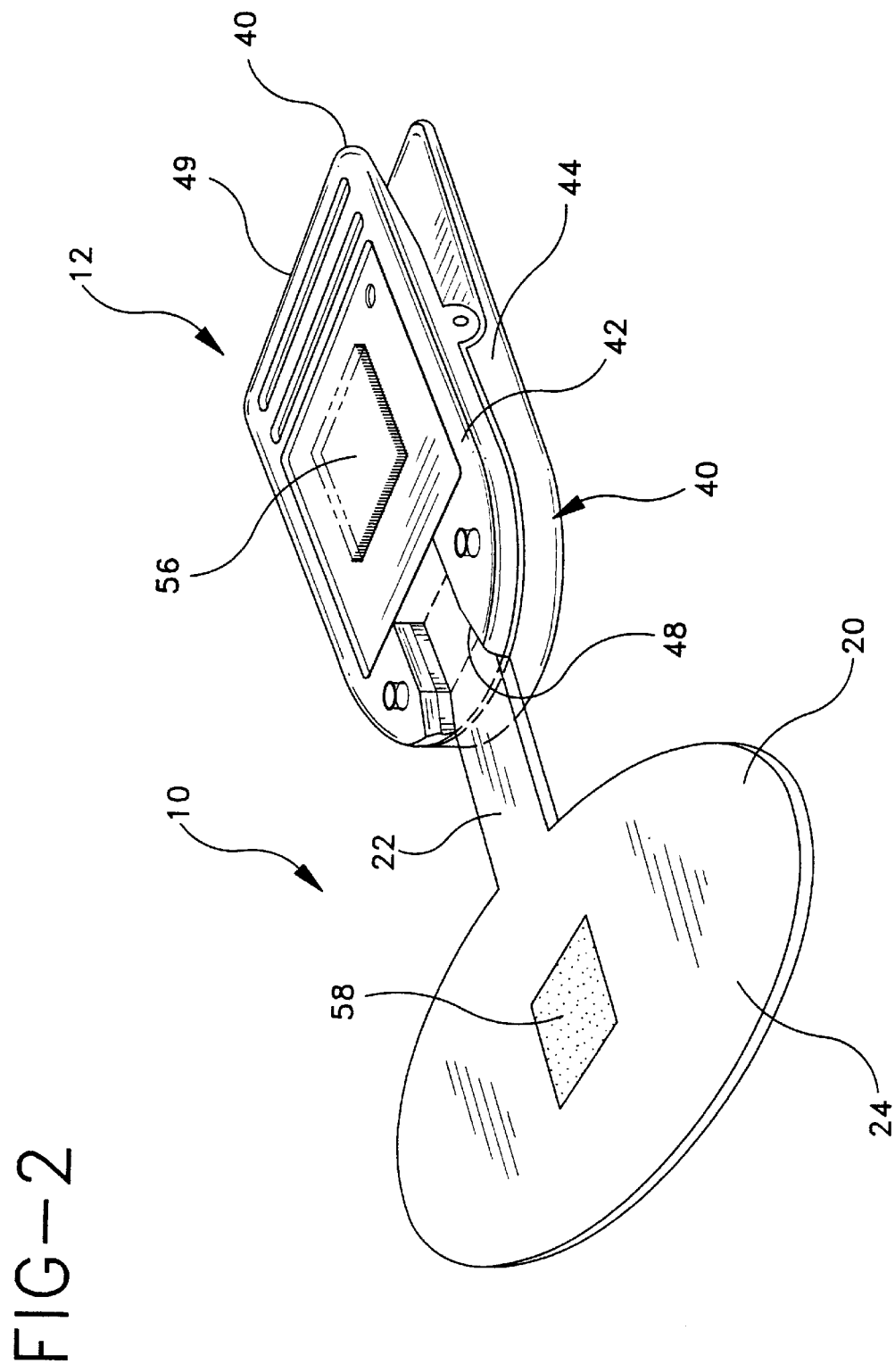
FIG. 2 is an perspective view of the patch interconnected with a controller.

The iontophoretic drug deliver system of the present invention is illustrated in FIGS. 1–3, with the patch generally designated 10.

Referring to FIGS. 1–3, the patch 10 of the present invention for use in the iontophoretic drug delivery system is electrically interconnectible to a controller 12 to form the operable system, with the patch, along with the controller, being attachable to the skin of a patient 14 (FIG. 3). The patch typically includes an active electrode assembly 16 and a counter electrode assembly 18. If a positively charged medicament is to be delivered to the skin 14, the medicament would be positioned in the active electrode assembly. In the preferred embodiment, a third or adjunct electrode assembly 19 is provided so that when delivering a local anesthetic such a Lidocaine, the local anesthetic may be delivered beneath the counter electrode as well as the active electrode as disclosed, for example, in co-pending patent application Ser. Nos. 08/129,887 filed Sep. 30, 1993 now abandoned and 08/129,627 filed Sep. 30, 1993 now abandoned, both entitled "IONTOPHORETIC DRUG DELIVERY SYSTEM AND METHOD FOR USING SAME," the disclosures of which are hereby incorporated by reference in their entirety.

As illustrated in FIGS. 2 and 3, the patch 10 is coupled to the controller 12 using well known means, for example, by printed flexible circuits, metal foils, wires, tabs or electrically conductive adhesives as disclosed for example in co-pending patent application Ser. No. 08/315,378, filed Sep. 30, 1994 now U.S. Pat. No. 5,498,235 entitled "IONTOPHORESIS ASSEMBLY INCLUDING PATCH/CONTROLLER ATTACHMENT," application Ser. No. 08/315,532 filed Sep. 30, 1994 pending, entitled "IONTOPHORESIS PATCH/CONTROLLER INTERCONNECTION USING A CONDUCTIVE ELASTOMER TO PROVIDE NOISE-FREE ELECTRICAL CONTACT BETWEEN PATCH AND CONTROLLER," application Ser. No. 08/315,533 filed Sep. 30, 1994 pending entitled "IONTOPHORESIS ASSEMBLY INCLUDING CLEANABLE ELECTRICAL CONTACTS," application Ser. No. 08/315,372 filed Sep. 30, 1994 pending entitled "APPARATUS AND METHOD FOR ENSURING COMPATIBILITY OF A REUSABLE IONTOPHORETIC CONTROLLER WITH AN IONTOPHORETIC PATCH," and application entitled "IONTOPHORETIC DRUG DELIVERY SYSTEM, INCLUDING REUSABLE DEVICE," filed Sep. 28, 1995, Ser. No. 08/534,897 now abandoned, the disclosures of which are hereby incorporated by reference in their entirety.

Referring to FIGS. 1 and 1A, the patch 10 is a generally planar flexible member and may be adhesively supported on the skin 14 of the patient (FIG. 3). The patch 10 includes an enlarged patch body 20 and an extending narrow tab 22. The patch body 20 includes opposed planar surfaces 24 and 26, with the planar surface 26 disposed for skin contact and including a drug reservoir 28 typically in a gel form which contains at least one drug, medicament, medicine or like active agents (hereinafter collectively referred to simply as drugs), preferably in an ionic form and possibly an adhesive layer 30. While the drug reservoir 28 is shown, any other known iontophoretic drug reservoir structure for placing a medicament in contact with the skin in an iontophoretic patch may be employed, as disclosed for example in patent application Ser. No. 08/129,222 filed Sep. 30, 1993 now abandoned entitled "IONTOPHORETIC DRUG DELIVERY DEVICE AND RESERVOIR AND METHOD OF MAKING SAME," the disclosure of which is hereby incorporated by reference in its entirety.

Each of the electrode assemblies 16 and 18 are positioned to be in contact with the skin once the patch 10 is secured, as shown in FIG. 3. The positioning of the electrode assemblies 16 and 18 is such that an electrical current path is established between the electrode assemblies 16 and 18 through the skin of the patient 14. A direct current source in combination with the electrode assemblies 16 and 18 and the patient's body 14 completes the circuit and generates an electric field across the body surface or skin to which the iontophoretic device is applied, with the drug reservoir 28 assuming the same charge as the ionized drug contained in the reservoir 28. Under the influence of electrical current passing from the electrode assembly 16 through the skin 14 to the electrode assembly 18, the drug contained in the drug reservoir 28 is transcutaneously delivered into the body of the patient by the process of iontophoresis.

Referring to FIGS. 1 and 2, the electrical current is supplied from the controller 12 to the electrode assemblies 16 and 18 on the patch via the electrical traces or leads 32 and 34 (FIG. 1). Each of the traces 32 and 34 may be one or more conductive paths extending from the electrode assemblies 16 and 18 to exposed conductive pads 36 positioned on a marginal edge of the patch tab 22. The pads 36 are positioned for electrical connection to the controller 12, which provides a source of electrical current as disclosed in patent application entitled "IONTOPHORETIC DRUG DELIVERY SYSTEM, INCLUDING REUSABLE DEVICE," filed Sep. 28, 1995, Ser. No. 08/534,897 now abandoned, the disclosure of which is hereby incorporated by reference in its entirety.

As previously indicated, when using a patch, preferably the patch 10 includes a means for insuring that a patch is not reused. Accordingly, as illustrated in FIGS. 1 and 1A, the patch 10 of the present invention, particularly the active electrode assembly 16, includes an additional counter electrode 60, which depending upon the ionic charge of the drug, will either act as a cathode or an anode. Thus, since the controller includes the electronics, and more particularly, the microprocessor, the controller upon being activated can deliver electrical current via conductive pad 36B along electrical trace 32B to the counter electrode 60, whereby the electrical current flows through the reservoir 28 surrounding the electrode assembly 16 to the electrode 62 along electrical trace 32A to conductive pad 36A. In this way, the electrode assembly 16 acts as a miniature iontophoretic device for a limited period of time during which a small amount of consumable material is transported to the electrode 62. Upon depletion of the consumable material, current will no longer be conducted along this electrical pathway. Then after a predetermined or preselected period of time sufficient to exceed the amount of time necessary to deplete electrode 60, electrical current is supplied along the pathway formed by electrical traces 34 and 32A.

Also, a resistor 70 may be situated along electrical trace 32B and interconnected through the controller 12 by electrical trace 72, in this way, the controller, among its other functions, may monitor the electrical voltage drop at the resistor 70, and if none is present, the controller will not fully activate the patch for delivery. In this way, it can be assured that the appropriate patch is with the appropriate controller as disclosed in patent application entitled "IONTOPHORETIC DRUG DELIVERY DEVICE HAVING AN IMPROVED CONTROLLER", filed Sep. 28, 1995 (Attorney Docket No. P-3173), the disclosure of which is hereby incorporated by reference in its entirety.

Also, in this way if the controller 12 is to be used with several different types of patches, it may monitor the electrical voltage at lead 72 and if it is within a predetermined range associated with a particular patch design, the controller can identify the type of patch connected and the corresponding current profile to be supplied. For example, a controller which is specifically programmed to provide current to a patch administering a specific medicament may need to operate at a certain current level for two hours in order to deliver the proper dosage when attached to one type of patch. In this way, the controller can be used with a variety of patches, and know which patch it is connected with, and likewise if an inappropriate patch is connected fail to activate the system. In this way, it can be assured that the controller is used with the appropriate patch.

To provide the user with the above information, the controller may include an indication means, such as LED's 80, to visually indicate to the user whether the system is operating and, when appropriate, that either a used patch is connected or an inappropriate patch is connected. The LED's are electrically coupled to the microprocessor so that information received and stored by the microprocessor can be transmitted via the LED's to a user, technician or healthcare professional. The stored data may also be transmitted by the LED's to a computer and displayed using any known means such as the display of the computer. The circuitry for performing the transmitting and receiving using LED's is well known to those skilled in the art and any such known circuitry may be used to accomplish this feature.

As a result of the above, the user can thus be assured that patches are not reused and that the appropriate patch is used to provide increase safety. Also in this way, costly methods and electronics to read serial numbers and the like can be eliminated reducing the cost of the controller.

The particular construction of the patch 10 is not essential to the present invention, and may be formed of woven or non-woven textiles or polymers or may be any other construction well known in the art. However, it is preferred that the electrode assemblies 16, 18, the electrical traces 32, 34 and the conductive pads be printed or otherwise formed on a polymeric substrate as disclosed, for example, in patent application Ser. No. 08/012,168 filed Feb, 2, 1993 now abandoned entitled "ACTIVE DRUG DELIVERY DEVICE, ELECTRODE AND METHOD FOR MAKING SAME," the disclosure of which is hereby incorporated by reference in its entirety.

As illustrated in FIGS. 2 and 3, the particular construction of the controller 12 is also not essential to the present invention and may include a controller housing 40 having an upper portion 42 and a lower portion 44 pivotably interconnected, with the portions being biased towards one another by a biasing means such as a spring 46. In this way, the housing 40 has a general clothespin shape and includes an biasingly openable front end 48 which accommodates the tab 22 of the patch 10 as disclosed in patent application entitled "IONTOPHORETIC DRUG DELIVERY SYSTEM, INCLUDING REUSABLE DEVICE," filed Sept. 28, 1995 Ser. No. 08/534,897 now abandoned, the disclosures of which are hereby incorporated by reference in their entirety. The housing 40 may further accommodate a connection array 50 adjacent the electronics 52 contained within the housing 40 and schematically shown in phantom in FIG. 2. The connection array 50 and the electronics 52 are preferably mounted to a common printed circuit board (not shown). The connection array 50 may include plural electrical terminals in electrical connection with the electronics 52 and may be connectible to the pads 36 of the tab 20 extending from the patch 10. As previously discussed, it may be appreciated that any suitable electrical interconnection device may be employed in accordance with the present invention.

Referring back to FIGS. 2 and 3, the controller 12 houses the electronics 52 that monitor and control the supply of electric current to the electrode assemblies 16 and 18 and the user interfaces. As is known in the art, the electrical components may include a source of electrical power such as a battery and additional electronic components, such as an application specific integrated circuit, a microprocessor, used to send a controlled electrical current to electrode assemblies 16 and 18. It should be appreciated that the particular electronics are not essential to the present invention, and may include, for example, those disclosed in co-pending patent application entitled "IONTOPHORETIC DRUG DELIVERY DEVICE HAVING AN IMPROVED CONTROLLER", filed Sep. 28, 1995 (Attorney Docket No. P-3173), application Ser. No. 08/315,377 filed Sep. 30, 1994 pending entitled "IONTOPHORETIC DRUG DELIVERY DEVICE HAVING IMPROVED CONTROLLER," application Ser. No. 08/315,372 filed Sep. 30, 1994 pending entitled "APPARATUS AND METHOD FOR ENSURING COMPATIBILITY OF A REUSABLE IONTOPHORETIC CONTROLLER WITH AN IONTOPHORETIC PATCH," and Application entitled "IONTOPHORETIC DRUG DELIVERY DEVICE HAVING HIGH-EFFICIENCY DC-TO-DC ENERGY CONVERSION CIRCUIT," filed Aug. 29, 1995 (Attorney Docket No. P-3171), the disclosures of which are hereby incorporated by reference in their entirety.

In the preferred embodiment, as illustrated in FIG. 2, the patch 10 may be easily interconnected with the controller 12 under thumb actuation to an open position exposing the connection array 50 for electrical connection with the pads 36 of the tab 20. Specifically, by pressing the rear end 49 of the housing with sufficient force to overcome the spring 46 to open front end 48 of housing 42. The tab 22 of the patch 10 may then be inserted in the open end, with the conductive pads 36 slidably engageable with the connection array 50 and the housing returned to a closed position by releasing the rear portion to cover the connection array 50 with the pads clamped or otherwise held therebetween.

In order to assure accurate alignment of the pads 36 of the tab 22 with the connection array 50 supported within the housing 40, the tab 20 is keyed to the housing 40. Specifically, the tab 22 includes an extending leg or like portion 38 on one side which is designed to fit in a corresponding notch 54 formed in at least one side of the front end 48 of the lower portion 42 of the housing 40. The notch 54 and the leg 38 are of similar shape so as to provide keyed accommodation of the tab 20 and the leg 38. The key structure included on both the housing front end 48 and the leg 38 insures proper orientation of the patch 10 and the controller 12 by preventing incorrect positioning of the patch 10 with respect to the controller 12. In the present embodiment, both the front end 48 and the notch 54, and the corresponding tab 22 and the leg 38 have a generally L-shaped cross-section, however, any other mating shape which would prevent incorrect alignment may be employed.

Referring to FIGS. 2 and 3, the patch 10 and the controller 12 may also include attachment means for permitting the releasable support of the controller 12 on the patch 10 after interconnection between the pads 36 and the connective array 50 is established. The surface 24 of patch 10, and the exposed upper portion 42 include cooperating fastening elements 56 and 58 thereon. In the present illustrative embodiment, the cooperating fastening elements 56, 58 include conventional hook and loop fasteners of the type sold under the trademark VELCRO. Any other cooperating type fasteners may be employed to achieve the same objective. One cooperating fastening element 56 is secured adhesively or otherwise to patch 10 on surface 24 while the other cooperating fastening member 58 is secured by adhesive or otherwise to the exposed surface of upper portion 42 of the housing 40. As described in further detail below, attachment of the mating hook and loop fasteners 56 or 58 provide removable support for controller 12 on patch 10. It may be appreciated by those skilled in the art that the patch and controller may take any known form. The only requirement is that the patch be capable of being physically and electrically connected to the controller 12.

Operation and Use

Having described one embodiment of the iontophoretic drug delivery system, including the disposable patch 10, of the present invention, its operation and use is described below.

As illustrated in FIG. 3, the patch 10 and the controller 12 may be adhesively secured to the skin 14 of the patient, with surface 26 of patch 10 placed in intimate contact with the skin 14 so that the electrode assemblies 16 and 18, as well as the drug containing reservoir 28, are supported in intimate contact with the skin 14. In order to iontophoretically deliver the medicament from reservoir 28 transcutaneously through the skin 14, the controller 12 is electrically connected to patch 10. The housing 40 is opened and the tab 22 of the patch 10 is inserted into the open front end 46 of the housing 40 (FIG. 2). As the controller 12 is designed to be maintained in electrical connection with the patch 10 during iontophoretic delivery of the drug contained in the reservoir 28, the controller 12 may then be fastened or otherwise attached to the patch 10 so that it will be conveniently retained on the skin of the patient (FIG. 3).

Thereafter upon activation of the system, electrical current will initially flow through trace 32B, electrode 60, electrode 62 and trace 32A, during which time, the consumable material on electrode 60 will preferably be exhausted and the controller will monitor whether electrical current is flowing, in which event the controller will then stop delivery of current along this pathway, and switch to delivering current through trace 34, electrode 64, electrode 62 and trace 32A, and the LED 80A would be preferably activated to indicate operation of the system. However, if the controller 12 did not detect the delivery of current during the initial period of time, the LED 80B would preferably be activated to indicate that the system was not operational.

At such time as a particular application of the drug delivery system is completed, the patch 10 and the controller 12 may be removed from the skin of the patient and disconnected from one anther. In this way, the used patch 10 can be disposed of and the controller 12 placed aside until the next administration of the drug is needed, when it can be reused with a new patch.

In the preferred embodiment, the patch 10 of the present invention contains Lidocaine (a local anesthetic) and Epinephrine or Adrenaline (vasoconstrictors). In this way, the device can be used for anesthetizing the applied area to minimize sensation from the insertion of a needle or the like. However, it should be appreciated that other substances suitable for being applied to the area may be utilized which are well known to those skilled in the art.

Active agent, drug, formulation, medication, medicament and active compound have been used herein to mean any ethical pharmaceutical compound or agent, such as therapeutic compounds, diagnostic agents, anesthetic agents and the like.

As is well known within the field, the device can be situated on the area of the patient to which the active agent is to be applied (the applied area) such as the skin and a voltage impressed across the electrode assemblies 16, 18 to cause electrical current to flow through the skin of the patient to drive or otherwise transport the drug preferably in the form of an ionic active agent into the skin and the tissue to be absorbed by the body of the patient. The electric field lines are sufficiently long, however, so that the active agent is transported to the desired depth within the skin, and possibly to the vasculature, to provide the desired effect, e.g., anesthetic, therapeutic or diagnostic. It should also be appreciated that the device of the present invention can be applied to other areas of the body such as mucus membranes depending upon the desired therapy and drugs to be delivered.

In addition, while the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

While the preferred embodiment of the present invention has been described so as to enable one skilled in the art to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A disposable patch for use in combination with a controller to form an operable iontophoretic drug delivery system, said disposable patch comprising:

a planar body portion including at least a first electrode assembly and a second electrode assembly, with each electrode assembly including at least one electrode; and means contained in one of said electrode assemblies for preventing reuse of a patch when interconnected with a controller, said means including a counter electrode adjacent to said electrode and in electrical communication with said electrode, and said electrode and said counter electrode being in contact with and adjacent to a reservoir;

said counter electrode including a material which upon electrical current flowing through said electrode and said counter electrode is consumed in a limited period of time so that upon depletion of the consumable material, current will no longer flow through said electrode and said counter electrode, whereby after electrical current has initially flowed through said electrode between said electrode and said counter electrode for a preselected period of time sufficient to exceed the amount of time necessary to deplete the consumable material of said counter electrode, electrical current is supplied to said first electrode assembly and said second electrode assembly to deliver the drug to the patient.

2. A disposable patch for use in combination with a controller to form an operable iontophoretic drug delivery system, said disposable patch comprising:

a planar body portion including at least a first electrode assembly and a second electrode assembly, with each electrode assembly including at least one electrode so that when electrical current flows between said first electrode assembly and said second electrode assembly at least one drug may be delivered to a patient iontophoretically;

means contained in one of said electrode assemblies for preventing reuse of a patch when interconnected with a controller, said means being situated adjacent to one of the electrodes contained in either said first or second electrode assembly and in electrical communication therewith, and said electrode and means being in contact with and adjacent to a reservoir;

said means including a material which upon electrical current flowing along a pathway interconnecting said electrode and said means is consumed in a period of time less than the time necessary to consume said other electrodes so that upon depletion of the consumable material, current will no longer flow along the electrical pathway connecting said electrode and said means, whereby after electrical current has initially flowed through said electrode assembly between said electrode and said means for a period of time sufficient to exceed the amount of time necessary to deplete the consumable material of said means, electrical current can flow between said first electrode assembly and said second electrode to deliver the drug to the patient.

3. The disposable patch defined in claim 2 wherein said means includes an additional electrode.

4. The disposable patch defined in claim 3 wherein at least one of said electrical traces interconnecting said electrode and said additional electrode includes a resistor situated along at least one of the electrical traces so that a controller may monitor the electrical voltage drop at the resistor, and if none is present, the controller will not fully activate the patch for delivering the drug to the patient.

5. The disposable patch defined in claim 2 further comprising electrical interconnection means for interconnecting said body portion with a controller.

6. The disposable patch defined in claim 5 wherein said body portion includes a tab having a plurality of electrical traces thereon in electrical communication with said electrode assemblies and said electrical interconnection means.

7. An iontophoretic drug delivery system including a disposable patch electrically interconnectible with a controller, the system comprising:

a drug-filled patch removably attachable to the skin of a patient for iontophoretically delivering at least one drug to the patient;

said patch including at least a first electrode assembly and a second electrode assembly, with each electrode assembly including at least one electrode so that when electrical current flows between said first electrode assembly and said second electrode assembly said drug may be delivered to the patient;

an additional electrode contained in one of said electrode assemblies for preventing reuse of a patch when interconnected with the controller, said additional electrode being situated adjacent to one of the electrodes contained in either said first or second electrode assembly and in electrical communication therewith, with said additional electrode including a material which upon electrical current flowing along a pathway interconnecting said electrode and said additional electrode is consumed in a limited period of time so that upon depletion of the consumable material of the additional electrode, current will no longer flow along the electrical pathway;

a controller removably, electrically connectible to said patch, the controller providing sufficient energy to said patch to drive the drug into the skin of the patient and said controller including electronic means for monitoring and controlling electrical current supplied to said patch so that electrical current can initially flow between said electrode assembly between said electrode and said additional electrode and after a period of time sufficient to exceed the amount of time necessary to deplete the consumable material of said additional electrode, the flow of electrical current can be switched to flow between said first electrode assembly and said second electrode to deliver the drug to the patient and the flow of electrical current can be prevented in the event the controller fails to detect the initial flow of current between the electrode and the additional electrode.

8. The iontophoretic drug delivery system defined in claim 7, wherein the controller includes an open front end and the patch includes a tab so that the patch is electrically connected to the controller by inserting the tab of the patch into the open front end of the controller.

9. A method for insuring that a patch is not reused, comprising the steps of:

electrically interconnecting a patch with a controller;

activating the controller so that electrical current can initially flow between an electrode and an additional electrode;

exhausting a consumable material of the additional electrode;

monitoring whether electrical current is flowing between the electrode and the additional electrode, and switching the flow of current after a predetermined period of time in the event current initially flowed through the electrode and the additional electrode so that current flows through the electrode and another electrode whereby at least one drug is delivered to a patient.

10. The method defined in claim 8, further comprising the step of preventing the flow of current if the initial flow of current between the electrode and the additional electrode is not detected.

11. The method defined in claim 8, wherein the controller is electrically connected to the patch by inserting a tab of the patch into an open front end of the controller.

* * * * *